(12) United States Patent
Ross

(10) Patent No.: US 7,009,394 B2
(45) Date of Patent: Mar. 7, 2006

(54) METHOD FOR ESTIMATING THE NUMBER OF NUCLEI OF A PRESELECTED ISOTOPE IN A MOLECULAR SPECIES FROM AND NMR SPECTRUM

(75) Inventor: Alfred Ross, Lörrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 4 days.

(21) Appl. No.: 10/983,077

(22) Filed: Nov. 5, 2004

(65) Prior Publication Data

US 2005/0114043 A1 May 26, 2005

(30) Foreign Application Priority Data

Nov. 7, 2003 (EP) .................................. 03025542

(51) Int. Cl.
*G01V 3/00* (2006.01)
(52) U.S. Cl. ....................................... 324/307; 324/309
(58) Field of Classification Search ................ 324/307, 324/309, 300, 318, 319, 322; 600/410; 436/173; 250/282
See application file for complete search history.

(56) References Cited

U.S. PATENT DOCUMENTS

| 4,081,742 A | | 3/1978 | Hofer et al. |
| 5,258,485 A | * | 11/1993 | Matsuo et al. ............... 528/206 |
| 5,834,620 A | * | 11/1998 | Eastmond et al. ............. 560/8 |

FOREIGN PATENT DOCUMENTS

FR   2 735 865   12/1996

OTHER PUBLICATIONS

Richard R. Ernst et al., Principles of Nuclear Magnetic Resonance in One and Two Dimensions, Clarendon Press, Oxford, 1987, pp. 92-157.
Laurent Barantin et al., A New Method for Absolute Quantitation of MRS Metabolites, Communications, pp. 179-182.
Reto Buchli et al., Comparison of Methods for the Determination of Absolute Metabolite Concentrations in Human Muscles, pp. 552-558.
Serge Akoka et al., Concentration Measurement by Proton NMR Using the Eretic Method, Anal. Chem. 1999, 2554-2557.

\* cited by examiner

*Primary Examiner*—Brij Shrivastav
(74) *Attorney, Agent, or Firm*—Cohen, Pontani, Lieberman & Pavane

(57) ABSTRACT

A method for estimating the number of nuclei of a preselected isotope in a molecular species starts with an NMR spectrum of a sample containing said molecular species as a predominant substance, said NMR spectrum comprising a plurality of signal peaks corresponding to said nuclei. By applying inclusion and ordering criteria one obtains a set of ordered signal peaks, the integration of which leads to a set of ordered integrals. Nested outer and inner iteration cycles are carried out, wherein for each cycle a trial number of nuclei is assigned to one of said ordered integrals whilst the other ordered integrals are rescaled accordingly and rounded to the next integer value, so as to yield a candidate total number of nuclei. An estimated total number of nuclei is obtained by taking the lowest one from the plurality of candidate total numbers of nuclei that have the highest number of occurrences.

10 Claims, 3 Drawing Sheets

METHOD FOR ESTIMATING THE NUMBER OF NUCLEI OF A PRESELECTED ISOTOPE IN A MOLECULAR SPECIES FROM AND NMR SPECTRUM

BACKGROUND OF THE INVENTION

1. Field of the Invention

The present invention relates to a method for estimating the number of nuclei of a preselected isotope in a molecular species from an NMR spectrum, to a use of said method and to a computer program product for performing said method.

2. Description of the Related Art

Nuclear magnetic resonance spectroscopy is a well-known technique that is extensively applied for qualitative and quantitative analysis of a large variety of samples. The technique generally involves recording a nuclear magnetic resonance spectrum, henceforth called NMR spectrum, under conditions that are selective for a preselected nuclear isotope with non-zero spin angular momentum, such as $^1H$, $^{13}C$ or many others. In general, an NMR spectrum obtained from a sample containing a molecular species comprises a plurality of signal peaks resulting from the nuclei of the preselected isotope. Each signal peak corresponds to a particular resonance frequency that is attributable to one or several nuclei experiencing a particular local magnetic field as a consequence of the particular molecular environment. Accordingly, the resonance frequency at which an NMR signal peak is observed, usually expressed in terms of the so-called chemical shift given in parts per million (ppm) with respect to a reference signal, is an indication of the molecular location of the nucleus or nuclei giving rise to the signal peak.

An important advantage of NMR spectroscopy as compared to other analytical techniques lies in the fact that under certain well-known conditions the integral of a signal peak is directly proportional to the number of resonating nuclei (see e.g. R. R. Ernst, G. Bodenhausen and A. Wokaun, Principles of Nuclear Magnetic Resonance in One and Two Dimensions, Oxford Science Publication, 1988, 91–157). Therefore, the integrals of the various signal peaks in an NMR spectrum reflect the number of nuclei contributing to each signal peak. This fact is routinely used as a guide for manual, i.e. non-automated interpretation of NMR spectra of unidentified molecular species, i.e. for qualitative analysis.

Moreover, NMR spectroscopy may also be used for quantitative analysis. Because of the above mentioned proportionality between integrals of signal peaks and numbers of resonating nuclei, the absolute integral of an NMR signal peak is directly related to the number of molecules containing the resonating nuclei that are present in the detection volume of the NMR spectrometer. However, the absolute integral of an NMR signal peak will generally depend on a host of experimental conditions. Quantitative analysis by means of NMR spectroscopy thus requires comparison of the measured signal integrals with an integral derived from a calibration signal.

Several methods for generating a suitable calibration signal are known in the art, as described e.g. in French Patent Application FR 2 735 865 A1. In particular, FR 2 735 865 A1 discloses a device and a method for quantitative analysis by NMR spectroscopy involving a synthetic NMR calibration signal produced by an electronic device. This technique has become known under the acronym "ERETIC" (standing for "Electronic REference To access In vivo Concentrations") as described in: L. Barantin, A. Le Pape and S. Akoka, A new method for absolute quantitation of MRS metabolites. Magn. Res. Methods Vol. 38 (1997) 179–182.

A fundamental problem in both qualitative and quantitative applications of NMR spectroscopy is caused by the fact that any NMR spectrum obtained in practice will deviate to some degree from the theoretical expectation. This discrepancy is mainly due to inevitable noise contributions, but also to other experimental influences such as field inhomogeneities, drifts and further effects. Moreover, solvent effects and exchange reactions, e.g. exchange of hydrogen ions when carrying out $^1H$-NMR spectroscopy may lead to inaccuracies in the determination of integrals. As a consequence, the integral of a signal peak as compared to others of the same molecular species will generally differ somewhat from the theoretical expectation. A further problem is caused by the so-called chemical shift degeneracy, which refers to a situation where nuclei at different locations within a molecular species have essentially identical chemical shifts and thus give rise to overlapping NMR signal peaks. These facts give rise to the following difficulties in qualitative and quantitative analysis by NMR-spectroscopy.

In qualitative analysis, the relative integrals of all the signal peaks in a particular NMR spectrum of a molecular species should be resealed, i.e. the integral of each signal peak should be multiplied by a common scaling factor so that each one of the resealed integrals is an integer number. The common scaling factor accounts for the detection sensitivity of the apparatus and for the concentration of said molecular species in the sample. The set of integer numbers thus obtained corresponds to the numbers of nuclei in the molecular species that give rise to the various signal peaks. In favorable cases of simple, non-congested spectra with small noise this procedure is successfully carried out in a straightforward fashion. Under less favorable conditions, however, calculating a set of integer rescaled intensities can result in a solution with unrealistic numbers of nuclei. For example, two signal peaks each resulting from one specific nucleus in a molecule should have the same signal integral, but finding an experimental integral ratio of 0.97/1.03 would suggest that the molecular species has 97 nuclei of the first sort and 103 nuclei of the second sort and thus would lead to an unacceptable interpretation of the NMR spectrum.

In quantitative analysis, the integral of a specific NMR signal peak of the molecular species to be determined is compared with the integral of a suitable calibration peak, which e.g. may be a synthetic NMR signal according to the ERETIC method or may be derived from a calibration substance of known concentration added to the sample. Obviously, this comparison must duly take into account the number of nuclei with identical chemical shift contributing to the specific signal peak. As in the case of qualitative analysis, any experimentally caused deviation from ideal signal integral would result in a corresponding error of the quantitative estimate. In the simple example mentioned above, depending on whether the first or the second integral is compared with the calibration integral, the result would be 0.97 or 1.03 times the true result.

In summary, the usefulness of NMR spectroscopy in qualitative and in quantitative analysis is limited by the fact that due to inevitable experimental inaccuracies and due to chemical shift degeneracy the number of nuclei of a preselected isotope in a molecular species is generally not directly available from an NMR spectrum of a sample containing said molecular species. Application of NMR spectroscopy in the fields mentioned above is also hampered by the fact that an automated determination of concentration and purity of samples is not known in the art. Automated analysis of samples with respect to number of nuclei is a prerequisite if NMR based quantitative and qualitative analysis is required at high throughput.

SUMMARY OF THE INVENTION

It is the principal object of the present invention to overcome the above mentioned difficulties and limitations of NMR spectroscopy for qualitative and quantitative analysis.

It is a further object of this invention to provide a method and its use for estimating the number of nuclei of a preselected isotope in a molecular species from an NMR spectrum of a sample containing said molecular species.

It is yet another object of this invention to provide a computer program product for estimating the number of nuclei of a preselected isotope in a molecular species from an NMR spectrum of a sample containing said molecular species.

The foregoing and further objects are achieved by the method defined in claim 1, the use defined in claim 9 and the computer program product defined in claim 10.

According to claim 1, there is provided a method for estimating the number of nuclei of a preselected isotope in a molecular species from an NMR spectrum of a sample containing said molecular species as a predominant substance. The preselected isotope may be any nuclear isotope suitable for NMR spectroscopy, including, but not limited to $^1H$, $^{13}C$ and $^{31}P$. The method is applicable to a broad range of molecular species contained in various types of samples. The method requires that the molecular species of interest give rise to a resolved NMR spectrum with a plurality of signal peaks, with a reasonable signal to noise ratio and without presence of overwhelming solvent signal. The method comprises the sequence of steps outlined in italic herein below and provided with explanatory comments.

a) Selecting from said plurality of signal peaks a set of included signal peaks that fulfil an inclusion criterion: The inclusion criterion will usually specify a spectral range, e.g. a range of chemical shifts, from which the signal peaks are selected. This range might have one or more excluded regions, e.g. a spectral region containing signal peak(s) originating from the solvent or from a known impurity, which are not intended for analysis.

b) Ordering said set of included signal peaks according to a preselected signal ordering criterion to obtain a set of ordered signal peaks: Typically, the signal peaks will be ordered according to their peak position (e.g. chemical shift at resonance) either in ascending or descending order, but any other arbitrary ordering could be applied as well c) Determining the integral of each one said ordered signal peaks to obtain a corresponding set of ordered integrals: The integration of NMR signal peaks is well known in the art and may be carried out with various means. It should be noted that the sequence of process steps b) and c) could also be interchanged.

d) Defining a set of mutually non-identical positive integers that do not exceed a preselected highest integer and ordering said set according to a preselected number ordering criterion to obtain a set of ordered integers: This operation generates an ordered set of integer numbers between 1 and a preselected highest integer $K_{max}$. For example, this may be the ordered set $\{1, 2, 3, 4, 5, \ldots, K_{max}\}$. However, any other ordering of the set members may be adopted and, moreover, the ordered set does not need to include all the integers between 1 and $K_{max}$, like e.g. in the ordered set $\{3, 27, 4, \ldots, 6, 89, 2\}$ with $K_{max}=89$.

e) Starting an outer iteration cycle by selecting the first one of said ordered integrals to obtain a selected integral: An outer iteration cycle is carried out for each one of said ordered integrals, beginning with the first one until all of said ordered integrals have been processed (see step m herein below). For a given outer iteration cycle, there will be exactly one currently selected integral.

f) Starting an inner iteration cycle by assigning to a running number the value of the first one of said ordered integers: An inner iteration cycle is carried out for each one of said ordered integers (see step l herein below); in a given inner iteration cycle, a running number is set equal to the current one of said ordered integers. This running number has the meaning of an assumed number of nuclei temporarily assigned to the currently selected integral.

g) Calculating a scaling factor given by the ratio of said running number to said currently selected integral: The scaling factor is based on the assumed number of nuclei temporarily assigned to the currently selected integral.

h) Multiplying with said scaling factor each one of said ordered integrals to produce a set of scaled integrals: With this operation, all integrals are rescaled according to the assumed number of nuclei temporarily assigned to the currently selected integral.

i) Rounding each one of said scaled integrals to the nearest integer value to produce a set of integerized scaled integrals: Due to inevitable inaccuracies of measurement and because the assumed number of nuclei temporarily assigned to the currently selected integral will in most cases be wrong, the scaled integrals will generally have non-integer values. The rounding operation produces a set of integrals with integer values.

j) Calculating the sum of said set of integerized scaled integrals to produce a candidate total number of nuclei: For the assumed number of nuclei temporarily assigned to the currently selected integral, summation of all the integerized scaled integrals yields a candidate total number of nuclei in the molecular species. At this point of the procedure, it is not yet established whether or not said candidate total number is an acceptable estimate for the true total number of nuclei.

k) Retrievably storing a result set corresponding to the instant inner iteration cycle, said stored result set containing at least said candidate total number of nuclei: This stored result set may be stored either temporarily or permanently, preferably on some suitable computer storage media, like kernel memory. Retrieval of the result set corresponding to a specified inner iteration cycle is ensured by appropriate encoding of the stored data, e.g. in the framework of a relational database.

l) Starting a further inner iteration cycle by setting the running number equal to the next one of said ordered integers, then assigning said running number to said selected integral and repeating steps g) to l) until all of said ordered integers have been processed: see step f) herein above.

m) Starting a further outer iteration cycle by selecting the next one of said ordered integrals and repeating steps f) to m) until all ordered integrals have been processed: see step e) herein above.

n) Determining from the plurality of said stored result sets the number of occurrences of each one of said candidate total numbers of nuclei: This operation yields a distribution of total numbers that may be plotted as a histogram showing how often each candidate total number of nuclei was found after completion of all the inner and outer iteration cycles.

o) Determining the highest number of occurrences in said distribution of total numbers.

p) Forming a set consisting of all the candidate total numbers of nuclei that have a number of occurrences equal to said highest number of occurrences: This set will always comprise at least one candidate total number of nuclei.

q) Obtaining an estimated total number of nuclei by taking the lowest one from said set of candidate total numbers of nuclei: This step ensures that the method yields a unique solution. In particular, solutions corresponding to trivial multiples of the simplest solution are thus eliminated.

The above defined method provides a simple and reliable, operationally well defined way of obtaining an estimate for the total number of nuclei from an essentially arbitrary NMR spectrum of a sample containing the molecular species of interest as a predominant substance.

According to claim 9, there is provided a use of the method according to this invention for quantitative determination of said molecular species in said sample.

According to claim 10, there is provided a computer program product comprising program code means stored on a computer readable medium for performing the method defined above when the computer program product is run on a computer system. For example, the computer program product might comprise an executable program stored on a compact disk or other suitable medium to be loaded in a personal computer.

Advantageous embodiments of the invention are disclosed in the dependent claims.

While one of the principal applications of the method according to this invention is directed at molecules with unknown total number of nuclei, the method is also applicable to molecules with known total number of nuclei, henceforth referred to as "nominal total number of nuclei". Under ideal conditions, the estimated total number of nuclei will be identical to the nominal total number of nuclei. However, under certain rather special circumstances the nominal total number of nuclei will be an integer multiple of the estimated total number of nuclei, e.g. twice as large. A discrepancy between the estimated total number of nuclei, or an integer multiple thereof, and the nominal total number of nuclei—if the latter is available—is indicative of certain non-ideal effects like the presence of an impurity with a substantial contribution to the NMR signal or the influence of exchange reactions on to the apparent integrals of the NMR signal peaks. In general, the presence of such non-ideal effects would require an intervention by an operator person. Accordingly, in the preferred embodiment according to claim 2, the method further comprises the steps of:

a) checking whether said estimated total number of nuclei or any integer multiple thereof up to a preselected largest integer multiplicator is identical to a nominal total number of nuclei of said molecular species; and b) if all of said identity checks are negative, issuing a warning notification.

In the preferred embodiment according to claim 3, each one of said stored result sets further comprises a global measure of deviation between the plurality of integerized scaled integrals and the plurality of scaled integrals obtained in the instant inner iteration cycle, the method further comprises the steps of:

a) taking all the result sets that correspond to said estimated total number of nuclei;

b) selecting the result set having the smallest global measure of deviation; and c) assigning to each one of said ordered signal peaks a corresponding partial number of nuclei obtained by taking, from said selected result set, the integerized scaled integral corresponding to said ordered signal peak.

In this way one obtains, in addition to the estimated total number of nuclei of the molecular species of interest, an estimate for the partial number of nuclei corresponding to each signal peak in the NMR spectrum. Such information is particularly useful for elucidation of the structural formula of the molecular species of interest. If there are more than one result set corresponding to the estimated total number of nuclei, a unique solution for the partial numbers of nuclei is chosen by selecting the result set with the smallest global measure of deviation, where the latter can be the sum of absolute deviations between integerized scaled integrals and scaled integrals, or it can be the root-mean-square-deviation or any other suitable statistical measure.

In the preferred embodiment according to claim 4, the method further comprises the steps of:

a) providing a calibration signal peak that does not fulfill said inclusion criterion and that corresponds to a specified number of nuclei of a calibration species;

b) integrating said calibration signal peak and dividing the result by said specified number of nuclei to obtain a calibration integral;

c) selecting a quantitation set consisting of at least one of said ordered signal peaks;

d) taking the sum of the ordered integrals corresponding to the ordered signal peaks of said quantitation set;

e) taking the sum of the estimated partial numbers of nuclei of the ordered signal peaks of said quantitation set;

f) obtaining a normalized sample integral defined as the ratio of said sum of ordered integrals and said sum of partial numbers of nuclei; and g) dividing said normalized sample integral by said calibration integral to obtain a relative concentration of the molecular species in the sample.

It should be emphasized that the calibration signal peak need not be acquired together with the NMR spectrum of the sample. In other words, the calibration signal could be extracted from another NMR spectrum taken on a well characterized reference sample. In any case, the calibration signal peak shall not fulfill said inclusion criterion, so as to ensure that it will not be taken into account when the outer and inner iteration cycles are carried out.

The above defined embodiment relies on the fact that under certain well-known conditions (see e.g. R. R. Ernst, G. Bodenhausen and A. Wokaun, loc. cit.) the integral of an NMR signal peak is directly proportional to the number of resonating nuclei. It is essential to provide a calibration signal peak that does not overlap with the signal peaks of the molecular species of interest. It will also be understood that the calibration signal peak should be known to correspond to a specified number of nuclei of a calibration species. By dividing the integral of the calibration peak by said specified of nuclei one obtains a calibration integral which serves as a reference for quantitative determination of said molecular species.

The quantitation set may comprise any one of said ordered integrals. In particular, it could include the entirety of ordered integrals, in which case the result of summation step e) would correspond to the estimated total number of nuclei of said preselected isotope in said molecular species.

Step g) yields as result a concentration of the molecular species in the sample expressed relative to that corresponding to the calibration signal peak.

An advantageous way of obtaining the normalized sample signal is defined in claim 5, according to which said quantitation set consists of the ordered signal peak corresponding to the selected integral associated with the selected result set. In other words, the quantitative determination is carried out by means of the signal peak associated with the smallest global measure of deviation.

In the particularly preferred embodiment defined in claim 6, said calibration signal peak is generated by means of an ERETIC-method, thus allowing to exploit the known advantages of a synthetic NMR calibration peak.

The method according to claim 7 further comprises the step of obtaining, from the set of ordered signal peaks and corresponding estimated partial numbers of nuclei, a substance set related to said molecular species and an impurity set related to impurity species contained in said sample, the substance set comprising the ordered signal peaks whose estimated partial number of nuclei is greater than zero and the impurity set comprising the ordered signal peaks whose estimated partial number of nuclei is equal to zero. The impurity set thus contains signal peaks that do not originate from the molecular species of interest. This information may be used to refine the inclusion criterion, i.e. one can repeat the above described procedure for estimating the number of nuclei with a refined set of included signal peaks in order to obtain a refined result.

The method according to claim 8 further comprises the steps of:
a) obtaining a substance related integral by taking either one integral or the sum of a plurality of integrals corresponding to the signal peaks of said substance set;
b) obtaining an impurity related integral by taking either one integral or the sum of a plurality of integrals corresponding to the signal peaks of said impurity set; and
c) comparing the impurity-related integral and the substance-related integral to obtain a measure for the relative number of nuclei of impurity species contained in the sample.

The above described embodiment can be simply used to obtain a relative measure for the impurity content in a series of samples all containing the same molecular species and a given type of impurity species with varying amount.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the Drawings.

The above mentioned and other features and objects of this invention and the manner of achieving them will become more apparent and this invention itself will be better understood by reference to the following description of various embodiments of this invention taken in conjunction with the accompanying drawings, wherein.

DETAILED DESCRIPTION OF THE PRESENTLY PREFERRED EMBODIMENTS

The exemplifications set out herein are not to be construed as limiting the scope of this disclosure or the scope of this invention in any manner.

Spectra shown were simulated by use of the ACD/HNMR Software package. All simulations were made for a nominal magnetic field strength of 14.1 Tesla using a default linewidth of 1 Hz for non-exchanging protons and of 5 Hz for exchanging protons. Each spectrum with a chemical shift range of 12.3 ppm was obtained from 16000 calculated spectral data points.

EXAMPLE 1

Figure 2:
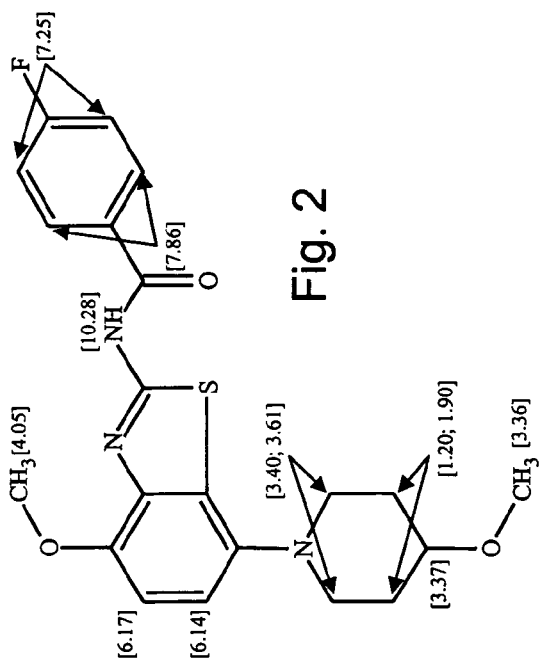
FIG. 2 shows a structural formula of molecular species A including chemical shifts (in ppm) of the hydrogen atoms.
Figure 1:
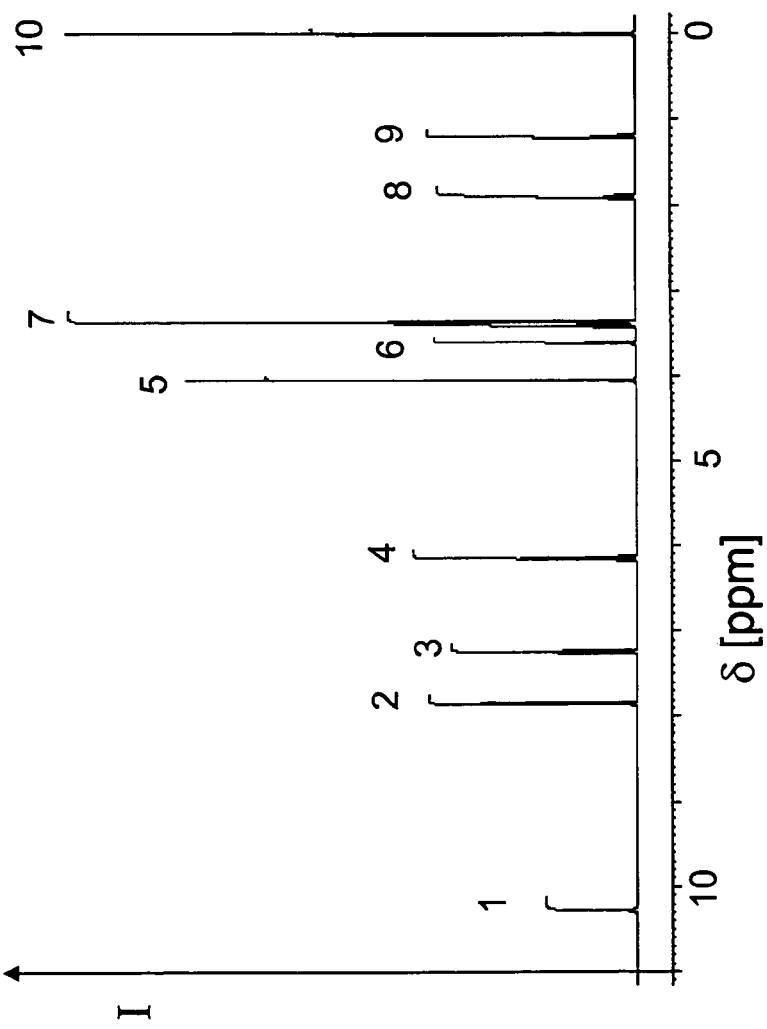
FIG. 1 shows a $^1$H-NMR spectrum of a first sample, containing molecular species A ($C_{21}H_{22}FN_3O_3S$) and an admixture of calibration compound tetramethyl silane (TMS), plotted as signal intensity I (in arbitrary units) vs. chemical shift $\delta$ (in ppm)

This example illustrates the application to an essentially pure sample of a species with unknown number of nuclei. FIG. 1 shows a $^1$H-NMR spectrum of a sample containing $C_{21}H_{22}FN_3O_3S$ (see FIG. 2), henceforth denoted as "molecular species A", and an admixture of tetramethyl silane (TMS), a well-known calibration substance for NMR spectroscopy. While it is known that molecular species A contains 22 protons, this information will not be used in the forthcoming procedure. The spectrum contains a plurality of signal peaks having chemical shifts $\delta$ in the range from about 0 to 11 ppm. While all these peaks have some multiplet structure, it is readily seen that the overall spectrum is made up of ten distinct signal peaks. In the present case, only signal peaks between 1 and 11 ppm are included for further analysis and define the set of included signal peaks P with members $\{P_1, P_2, \ldots, P_9\}$. The signal at 0 ppm is known to originate from TMS and will be used in Example 3 for calibration purposes, but is not part of the set of included signal peaks in the present example. The set P is ordered according to peak position by assigning a peak number to each included signal peak, thus forming the set of ordered signal peaks Π with members $\{\Pi_1, \Pi_2, \ldots \Pi_9\}$. The integral of each ordered signal peak is determined by a standard numerical integration procedure resulting in the set of ordered integrals S with members $\{S_1, S_2, \ldots, S_9\}$. This concludes the initial procedure of preparing a set of raw data as listed in Table 1.

TABLE 1

Set of ordered integrals S of Example 1

| Peak no. $\Pi_j$ | Chemical shift δ [ppm] | Ordered Integral $S_j$ [a. u.] |
|---|---|---|
| 1 | 10.279 | 4.335 |
| 2 | 7.860 | 9.122 |
| 3 | 7.255 | 9.368 |
| 4 | 6.157 | 9.054 |
| 5 | 4.054 | 13.667 |
| 6 | 3.615 | 9.228 |
| 7 | 3.357 | 27.770 |
| 8 | 1.908 | 8.710 |
| 9 | 1.204 | 8.746 |

The procedure for estimating the number of $^1$H-nuclei (henceforth denoted as "protons" in molecular species A is now explained. It should be emphasized that no information about the number of protons (which is known to be 22 in this case) is used for carrying out this procedure.

One starts by defining a preselected highest integer $K_{max}$ that should be chosen as an upper limit for the unknown number of protons. A reasonable value for Kmax can usually be obtained from additional chemical information about the molecular species of interest, e.g. from knowledge about how the molecular species was synthesized from known reactants. Alternatively, $K_{max}$ may be extracted from combustion analysis or some other routine analytical method. For simplicity, it will be assumed here that $K_{max}$=50, but higher values could be chosen in practice. Subsequently, one defines an ordered set of mutually non-identical positive integers K that do not exceed $K_{max}$, for example the ordered set K={1, 2, 3, 4, 5, . . . , 50} with members $\{K_1, K_2, \ldots K_{50}\}$.

An outer iteration cycle is now started by selecting the first ordered integral $S_1$, related to the peak $\Pi_1$. Moreover, an inner iteration cycle is started by assigning to a running number the value of the first element $K_1$ of the above defined set of positive integers K. Then a scaling factor $s(S_1, K_1)$ of the instant outer and inner iteration cycle is calculated as the ratio of said selected positive integer $K_1$ and the instant selected integral $S_1$. Accordingly, one obtains $s(S_1, K_1)=1/4.335 \approx 0.23$. Each one of the ordered integrals $S_j$ in S is then multiplied with this instant scaling factor, thus leading to a set of scaled signals C with members $\{C_1, C_2, \ldots, C_9\}$. With this operation, the set of ordered integrals is rescaled in accordance with the instant assumption that the ordered integral $S_1$ is associated with $K_1$ protons. Thereafter, each one of said scaled integrals $C_j$ is rounded to the nearest integer value to produce a set of integerized scaled integrals I with members $\{I_1, I_2, \ldots I_9\}$. Summation of all the integerized scaled integrals then yields a candidate total number of protons M for the instant outer and inner iteration cycle. A result set $R(S_1, K_1)$ containing at least said candidate total number of protons is stored for further processing. The outcome of the foregoing steps is illustrated in Table 2.

TABLE 2

Outcome of first outer and inner iteration cycle

| Peak No. $\Pi_j$ | Chemical shift δ [ppm] | $S_j$ [a. u.] | $C_j$ [a. u.] | $I_j$ |
|---|---|---|---|---|
| 1 | 10.279 | 4.335 | 1.000 | 1 |
| 2 | 7.860 | 9.122 | 2.104 | 2 |
| 3 | 7.255 | 9.368 | 2.161 | 2 |
| 4 | 6.157 | 9.054 | 2.089 | 2 |
| 5 | 4.054 | 13.66 | 3.153 | 3 |
| 6 | 3.615 | 9.228 | 2.129 | 2 |
| 7 | 3.357 | 27.77 | 6.406 | 6 |
| 8 | 1.908 | 8.710 | 2.009 | 2 |
| 9 | 1.204 | 8.746 | 2.018 | 2 |

Incidentally, summation of integerized scaled integrals $I_j$ yields a candidate total number of protons M of 22, which happens to be the correct number of protons of species A. However, this is of no relevance in the present example in which it is assumed that the number of protons is not known.

The procedure is then continued by carrying out the second inner iteration cycle of the first outer iteration cycle. With the running number set equal to $K_2$ all steps outlined above are repeated. Basically, this means assigning two protons to the ordered integral $S_1$. This finally leads to a candidate total number of protons M of 45 stored in $R(S_1, K_1)$. Further inner iteration cycles are carried out all the way up to $K_{50}$, yielding ever-larger candidate total numbers of protons.

Subsequently, the next outer iteration cycle is started by selecting $S_2$ out of the set of ordered integrals S, starting with $K_1$, i.e. by assigning one proton to the integral $S_2$, and continuing all the way to $K_{50}$. Further outer and inner iteration cycles are carried out until all the integrals of the set S have been processed. With 9 integrals and 50 members of K, this requires a total number of 4'500 iterations.

From the plurality of stored results R, one determines the number of occurrences f(M) of each one of said candidate total numbers of protons M (which is obtained from the sum of all integerized scaled integrals $I_i$ in a given inner iteration cycle, see above). For this purpose, it is appropriate to sort the result sets and order these by increasing value of the candidate total number of protons M, as shown in Table 3 for values up to 23.

From Table 3 it is seen e.g. that there is only one solution yielding a candidate total number of protons equal to 1, whereas there are four solutions for 10 protons. The candidate total number of protons with the highest number of occurrences is 22 (shown with bold print in Table 3), here f(22) equals 9. It must be noted that in this case 9 is the highest possible number of occurrences, as 9 ordered integral values were used for the analysis. This means that for each integral in the set S a number of protons can be found resulting in a total of 22 protons in species A.

TABLE 3

Results sorted by increasing candidate total number of protons

| Candidate total number of protons $\Delta_M(\Pi_k) = \sum_{j=1}^{9}|C_j - I_j|$ Selected peak $\Pi_k$ [a. u.] | Chemical shift δ [ppm] | Number of protons assigned to selected peak | Sum of scaled signals $\Delta_M(\Pi_k) = \sum_{j=1}^{9} \mathcal{A}C_j(\Pi I_j)$ [a. u.] | Sum of absolute deviations from integer values $= \sum_{j=1}^{9}|C_j - I_j|$ [a. u.] |
|---|---|---|---|---|
| 1   | 7 | 3.357  | 1 | 3.6   | 2.601 |
| 9   | 5 | 4.054  | 1 | 7.32  | 2.381 |
| 9   | 7 | 3.357  | 2 | 7.2   | 2.422 |
| 10  | 7 | 3.357  | 3 | 10.8  | 1.111 |
| 10  | 6 | 3.615  | 1 | 10.84 | 1.114 |
| 10  | 2 | 7.860  | 1 | 10.96 | 1.15  |
| 10  | 3 | 7.255  | 1 | 10.67 | 1.169 |
| 11  | 4 | 6.157  | 1 | 11.04 | 1.17  |
| 11  | 9 | 1.204  | 1 | 11.43 | 1.317 |
| 11  | 8 | 1.908  | 1 | 11.48 | 1.343 |
| 13  | 7 | 3.357  | 4 | 14.4  | 2.218 |
| 13  | 5 | 4.054  | 2 | 14.63 | 2.365 |
| 20  | 7 | 3.357  | 5 | 18    | 2.916 |
| 22 | 2 | 7.860 | 2 | 21.92 | 0.407 |
| 22 | 5 | 4.054 | 3 | 21.95 | 0.41 |
| 22 | 6 | 3.615 | 2 | 21.67 | 0.425 |
| 22 | 7 | 3.357 | 6 | 21.61 | 0.442 |
| 22 | 4 | 6.157 | 2 | 22.09 | 0.463 |
| 22 | 3 | 7.255 | 2 | 21.35 | 0.651 |
| 22 | 9 | 1.204 | 2 | 22.87 | 0.902 |
| 22 | 8 | 1.908 | 2 | 22.96 | 0.972 |
| 22 | 1 | 10.279| 1 | 23.07 | 1.068 |
| 23  | 7 | 3.357  | 7 | 25.21 | 2.207 |

Figure 3:
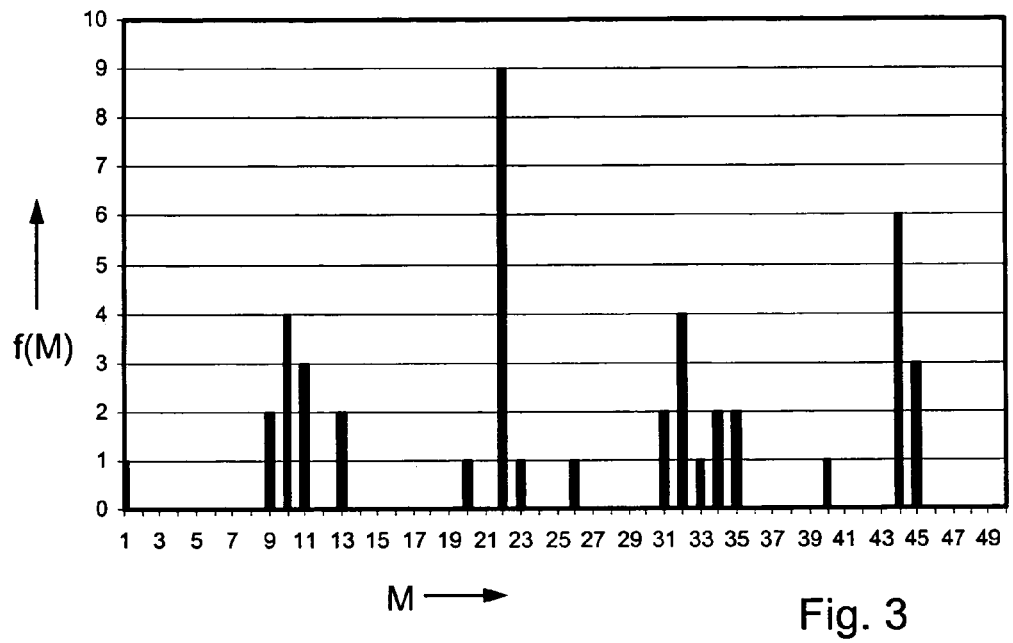
FIG. 3 shows a histogram of the candidate total numbers of $^1$H-nuclei determined from the spectrum of FIG. 1, plotted as number of occurrences f(M) vs. candidate total number of nuclei M.

A graphical representation of the number of occurrences f(M) plotted vs. the candidate total number of protons M in the range 1 to 50 is shown in FIG. 3. Inspection of the complete set of results shows that M equal to 22 is indeed the solution with the highest number of occurrences. Therefore, the estimated total number of protons in this example is equal to $M_{est}=22$, which is in full agreement with the nominal total number of protons of molecular species A.

Returning to Table 3, the rightmost column shows for each result set a corresponding global measure of deviation $\Delta_M(\Pi_k)$, defined here as the sum of absolute deviations from integer values for the result set with given candidate total number of protons M and given selected peak $\Pi_k$. In other words, for a given result set one calculates for every ordered integral in the set S the absolute deviation between scaled integral and integerized scaled integral, and subsequently the sum of these absolute deviations is taken for the given result set. Other statistical measures such as the sum of root-mean-square deviations between $C_j$ and $I_j$ could be taken alternatively. Among the result sets that correspond to said estimated total number of nuclei, i.e. the result sets with M=22, it is found that the result set associated with the selected peak j=2 has the smallest global measure of deviation, namely $\Delta_{22}(\Pi_2)=0.407$. This result set corresponds to assigning a number of 2 protons to peak no. 2, with the outcome shown in Table 4. The row shown with bold print in Table 4 reflects the instant assumption that peak no. 2 is associated with 2 protons; the integerized scaled integrals shown in the rightmost column of Table 4 represent the partial number of nuclei that is attributed to each peak. Obviously, the sum of partial numbers of nuclei is 22 and thus corresponds to the estimated total number of nuclei.

TABLE 4

Iteration cycle for selected peak $\Pi_2$, assuming K = 2 protons

| Peak No. $\Pi_j$ | Chemical shift δ [ppm] | $S_j$ [a. u.] | $C_j$ [a. u.] | $I_j$ |
|---|---|---|---|---|
| 1 | 10.279 | 4.335  | 0.950 | 1 |
| 2 | 7.860  | 9.122  | 2.000 | 2 |
| 3 | 7.255  | 9.368  | 2.054 | 2 |
| 4 | 6.157  | 9.054  | 1.985 | 2 |
| 5 | 4.054  | 13.66  | 2.996 | 3 |
| 6 | 3.615  | 9.228  | 2.023 | 2 |
| 7 | 3.357  | 27.77  | 6.089 | 6 |
| 8 | 1.908  | 8.710  | 1.910 | 2 |
| 9 | 1.204  | 8.746  | 1.918 | 2 |

EXAMPLE 2

Figure 4:
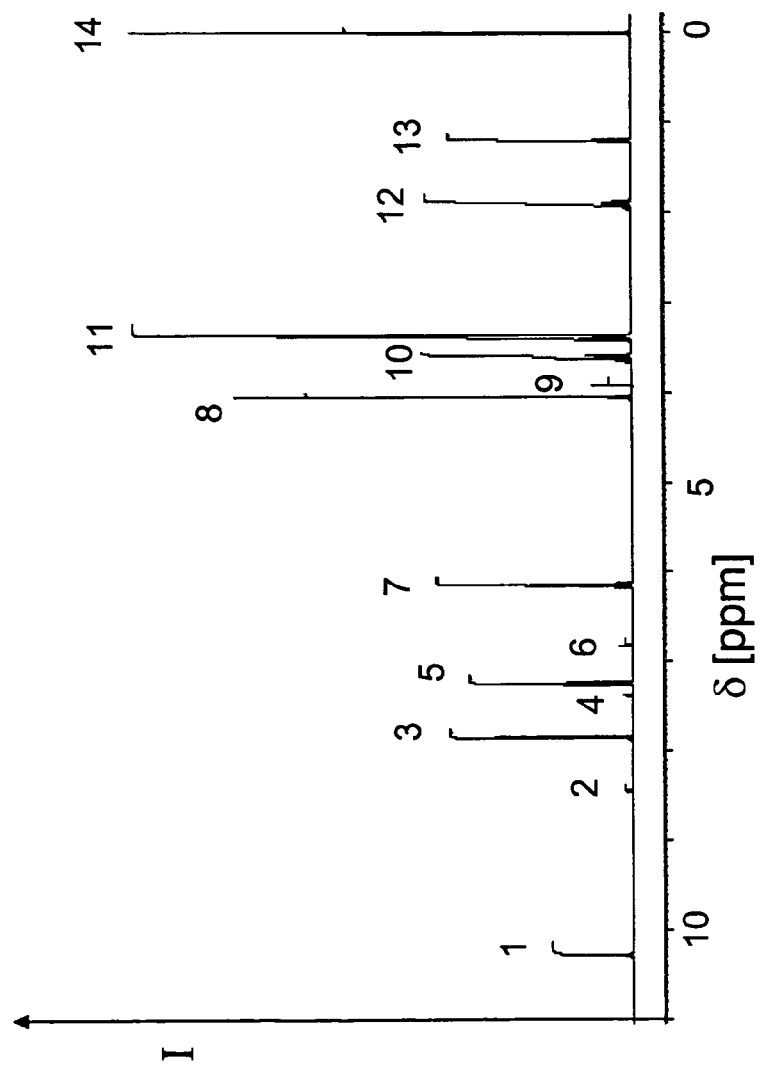
FIG. 4 shows a $^1$H-NMR spectrum of a second sample, containing molecular species A, an admixture of calibration compound TMS and an admixture of molecular species B ($C_{13}H_{14}ClN_3O_3$), plotted as signal intensity I (in arbitrary units) vs. chemical shift $\delta$ (in ppm)

This example illustrates the application to a contaminated sample containing a predominant molecular species A but also a substantial contribution of an impurity. FIG. 4 shows the $^1$H-NMR spectrum of a second sample, containing molecular species A, the calibration compound TMS and an admixture of 10% of $C_{13}H_{14}ClN_3O_3$, henceforth denoted as "molecular species B". For the purpose of this example, molecular species B is considered to be an unknown impurity in the sample.

Again, only signal peaks in the range of chemical shifts from 1 to 11 ppm are taken to build the set of included signal peaks, which is ordered according to peak position, thus forming the set Π of ordered signal peaks. After integration of each ordered signal peak the set of ordered integrals $S=\{S_1, S_2, \ldots, S_{13}\}$, listed in Table 5 is obtained. In contrast to the Example 1, there are now 13 ordered integrals instead of 9; peak no. 14 originates from TMS and does not belong to the set of included signal peaks. At first glance it appears that peaks no. 2, 4, 6 and 9 are considerably weaker that the other peaks and thus might be due to an impurity, but this fact is not exploited in the present procedure.

TABLE 5

Set of ordered integrals of Example 2

| Peak no. $\Pi_j$ | Chemical shift $\delta$ [ppm] | Ordered integrals $S_i$ [a. u.] |
|---|---|---|
| 1 | 10.300 | 3.992 |
| 2 | 8.470 | 0.421 |
| 3 | 7.881 | 8.171 |
| 4 | 7.438 | 0.432 |
| 5 | 7.243 | 8.504 |
| 6 | 6.849 | 0.328 |
| 7 | 6.179 | 9.892 |
| 8 | 4.117 | 12.772 |
| 9 | 3.902 | 1.488 |
| 10 | 3.666 | 10.179 |
| 11 | 3.336 | 25.398 |
| 12 | 1.939 | 10.282 |
| 13 | 1.225 | 8.137 |

Figure 6:
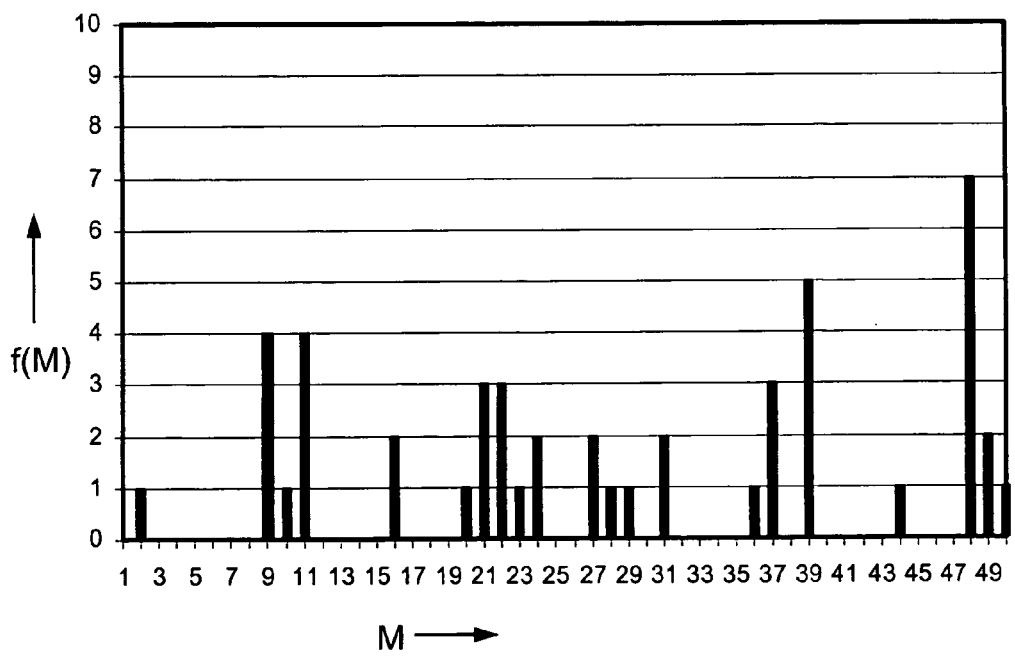
FIG. 6 shows a histogram of the candidate total numbers of $^1$H-nuclei determined from the spectrum of FIG. 4, plotted as number of occurrences f(M) vs. candidate total number of nuclei M.
Figure 5:
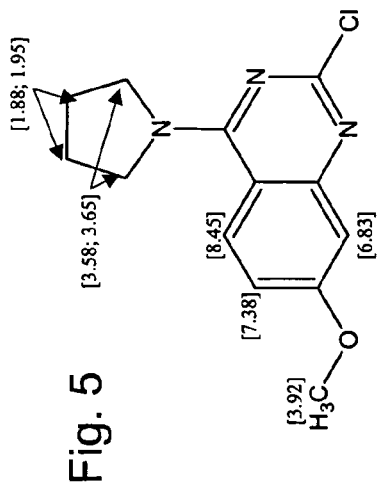
FIG. 5 shows a structural formula of molecular species B including chemical shifts (in ppm) of the hydrogen atoms.

After performing the steps outlined above for Example 1 and using $K_{max}=50$ and sorting the results by increasing value of the candidate total number of protons, one obtains the data shown in FIG. 6 as histogram for the result sets up to M=50. In this example, the candidate total number of protons M=22 occurs only three times, and the highest occurrence is found for M=48, with f(48)=7. In other words, the estimated total number of protons $M_{est}$=48 is not identical to the nominal number of protons $M_{nom}$=22. In addition f(48) is not equal to 13, which would be expected if a consistent interpretation of all integrals with a single compound were possible. Obviously, these discrepancies are caused by the non-negligible signal contributions from the impurity species B.

Advantageously, whenever a discrepancy between the estimated and the nominal total number of protons is found, a warning notification is issued. For example, the warning notification may consist of an error message being displayed to alert the operator that the sample is likely to be contaminated or otherwise corrupted. In favorable cases, it may be possible for the operator to discard a certain number of signal peaks, particularly the weakest ones, and to repeat the procedure for estimating the number of nuclei by using a correspondingly restricted inclusion criterion.

EXAMPLE 3

In this example, reference is made to the results of Example 1, which are used to carry out a quantitative determination of molecular species A in the sample at issue. Such determination relies on the fact that the calibration compound TMS contains 12 protons per molecule. Moreover, the method exploits the total or partial numbers of nuclei determined for species A and the relative magnitudes of NMR signal integrals found for A and TMS. The integrals mentioned below are all expressed in arbitrary units which, however, are the same arbitrary units for all the integrals from a given NMR spectrum.

A calibration integral $Y_{TMS}$ is obtained by integrating peak no. 14, which originates from TMS, and dividing by the number of protons, which is known to be 12. In the present case, this leads to a calibration integral $Y_{TMS}$=15.23/12=1.27.

Moreover, a quantitation set is defined which consists of at least one of the ordered signal peaks of species A. A normalized sample integral is then obtained by taking the sum of ordered integrals of the quantitation set divided by the sum of the estimated partial numbers of nuclei corresponding thereto. For the sake of simplicity, the quantitation set is taken to consist of all the selected peaks, i.e. peaks no. 1 through 9. One thus obtains the normalized sample integral by taking the sum of the values $S_j$ of the third column in Table 2 and dividing by the sum of estimated partial numbers of nuclei, which is 22. This leads to a normalized sample integral of 100/22=4.55.

Finally, one divides said normalized sample integral by said calibration integral to obtain a relative concentration of the molecular species in the sample. In the present example, this leads to a relative concentration of species A in relation to the calibration compound TMS of 4.55/1.27=3.58. Obviously this means that if the absolute concentration of the calibration compound is known to be $C_{TMS}$, then the absolute concentration of species A is $C_A$=3.58 $C_{TMS}$.

Instead of taking the signal of a calibration substance added to the sample, one can use an electronic calibration signal according to the ERETIC method. If so, it is necessary to carry out an initial calibration procedure so as to establish what proton concentration is equivalent to a given ERETIC signal.

LIST OF REFERENCE SYMBOLS f(M) number of occurrences of M
$K_i$ positive integer
$K_{max}$ preselected highest integer
M candidate total number of protons
$M_{est}$ total number of protons
P peak no. (for included peaks)
R result set
s(P, n) scaling factor
$S_j$ integrated signal
$\delta$ chemical shift
$I_j$ integerized scaled integral
$\Pi_j$ ordered signal peak
$C_j$ scaled integral
$\Delta_M (\Pi_k)$ global measure of deviation Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method for estimating the number of nuclei of a preselected isotope in a molecular species from an NMR spectrum of a sample containing said molecular species as a predominant substance, said NMR spectrum comprising a plurality of signal peaks corresponding to said nuclei, the method comprising the steps of:

a) selecting from said plurality of signal peaks a set of included signal peaks that fulfill an inclusion criterion;

b) ordering said set of included signal peaks according to a preselected signal ordering criterion to obtain a set of corresponding ordered signal peaks;

c) determining the integral of each one of said ordered signal peaks to obtain a corresponding set of ordered integrals;

d) defining a set of mutually non-identical positive integers that do not exceed a preselected highest integer and ordering said set according to a preselected number ordering criterion to obtain a set of ordered integers;

e) starting an outer iteration cycle by selecting the first one of said ordered integrals to obtain a selected integral;

f) starting an inner iteration cycle by assigning to a running number the value of the first one of said ordered integers;

g) calculating a scaling factor given by the ratio of said running number to said currently selected integral;

h) multiplying with said scaling factor each one of said ordered integrals to produce a set of scaled integrals;

i) rounding each one of said scaled integrals to the nearest integer value to produce a set of integerized scaled integrals;

j) calculating the sum of said set of integerized scaled integrals to produce a candidate total number of nuclei;

k) retrievably storing a result set corresponding to the instant inner iteration cycle, said stored result set containing at least said candidate total number of nuclei;

l) starting a further inner iteration cycle by setting the running number equal to the next one of said ordered integers, then assigning said running number to said selected integral and repeating steps g) to l) until all of said ordered integers have been processed;

m) starting a further outer iteration cycle by selecting the next one of said ordered integrals and repeating steps f) to m) until all ordered integrals have been processed;

n) determining from the plurality of said stored result sets the number of occurrences of each one of said candidate total numbers of nuclei;

o) determining the highest number of occurrences;

p) forming a set consisting of all the candidate total numbers of nuclei that have a number of occurrences equal to said highest number of occurrences; and q) obtaining an estimated total number of nuclei by taking the lowest one from said set of candidate total numbers of nuclei.

2. The method according to claim 1, further comprising the steps of:

checking whether said estimated total number of nuclei or any integer multiple thereof up to a preselected largest integer multiplicator is identical to a nominal total number of nuclei of said molecular species; and if all of said identity checks are negative, issuing a warning notification.

3. The method according to claim 1 or 2, wherein each one of said stored result sets further comprises a global measure of deviation between the plurality of integerized scaled integrals and the plurality of scaled integrals obtained in the instant inner iteration cycle, the method further comprising the steps of:

taking all the result sets that correspond to said estimated total number of nuclei;

selecting the result set having the smallest global measure of deviation; and assigning to each one of said ordered signal peaks a corresponding partial number of nuclei obtained by taking, from said selected result set, the integerized scaled integral corresponding to said ordered signal peak.

4. The method according to claim 3, further comprising the steps of:

providing a calibration signal peak that does not fulfill said inclusion criterion and that corresponds to a specified number of nuclei of a calibration species;

integrating said calibration signal peak and dividing the result by said specified number of nuclei to obtain a calibration integral;

selecting a quantitation set consisting of at least one of said ordered signal peaks;

taking the sum of the ordered integrals corresponding to the ordered signal peaks of said quantitation set;

taking the sum of the estimated partial numbers of nuclei of the ordered signal peaks of said quantitation set;

obtaining a normalized sample integral defined as the ratio of said sum of ordered integrals and said sum of partial numbers of nuclei; and dividing said normalized sample integral by said calibration integral to obtain a relative concentration of the molecular species in the sample.

5. The method according to claim 4, wherein said quantitation set consists of the ordered signal peak corresponding to the selected integral associated with the selected result set.

6. The method according to claim 4 or 5, wherein said calibration signal peak is generated by means of an ERETIC-method.

7. The method according to claim 3 to 6, further comprising the step of obtaining, from the set of ordered signal peaks and corresponding estimated partial numbers of nuclei, a substance set related to said molecular species and an impurity set related to impurity species contained in said sample, the substance set comprising the ordered signal peaks whose estimated partial number of nuclei is greater than zero and the impurity set comprising the ordered signal peaks whose estimated partial number of nuclei is equal to zero.

8. The method according to claim 7, further comprising the steps of:

obtaining a substance related integral by taking either one integral or the sum of a plurality of integrals corresponding to the signal peaks of said substance set;

obtaining an impurity related integral by taking either one integral or the sum of a plurality of integrals corresponding to the signal peaks of said impurity set; and comparing the impurity-related integral and the substance-related integral to obtain a measure for the relative number of nuclei of impurity species contained in the sample.

9. Use of the method according to claim 4 to 6 for quantitative determination of said molecular species in said sample.

10. A computer program product comprising program code means stored on a computer readable medium for performing the method according to any one of claim 1 to 8 when the computer program product is run on a computer system.

* * * * *